US012318167B2

(12) United States Patent
Braaf et al.

(10) Patent No.: US 12,318,167 B2
(45) Date of Patent: Jun. 3, 2025

(54) ASSEMBLY FOR CARRYING OUT AN OPTICAL COHERENCE TOMOGRAPHY

(71) Applicant: Heidelberg Engineering Gmbh, Heidelberg (DE)

(72) Inventors: Boy Braaf, Heidelberg (DE); Silke Aumann, Pfungstadt (DE); Björn Martensen, Lübeck (DE); Lisa Kutzner, Berlin (DE); Andreas Fritz, Lübeck (DE)

(73) Assignee: Heidelberg Engineering GmbH, Heidelberg (DE)

( * ) Notice: Subject to any disclaimer, the term of this patent is extended or adjusted under 35 U.S.C. 154(b) by 171 days.

(21) Appl. No.: 17/928,296

(22) PCT Filed: Apr. 8, 2021

(86) PCT No.: PCT/EP2021/059129
§ 371 (c)(1),
(2) Date: Nov. 29, 2022

(87) PCT Pub. No.: WO2021/244794
PCT Pub. Date: Dec. 9, 2021

(65) Prior Publication Data
US 2023/0210376 A1 Jul. 6, 2023

(30) Foreign Application Priority Data

Jun. 2, 2020 (DE) ...................... 10 2020 114 610.8

(51) Int. Cl.
*A61B 5/00* (2006.01)
*A61B 3/10* (2006.01)
(52) U.S. Cl.
CPC .............. *A61B 5/0066* (2013.01); *A61B 3/10* (2013.01)

(58) Field of Classification Search
CPC ...... A61B 5/0066; A61B 3/10; G01B 9/0205; G01B 2290/70; G01B 9/02091; G01B 9/02058
See application file for complete search history.

(56) References Cited

U.S. PATENT DOCUMENTS

| | | |
|---|---|---|
| 2003/0174339 A1 | 9/2003 | Feldchtein et al. |
| 2004/0126048 A1 | 7/2004 | Dave et al. |

(Continued)

FOREIGN PATENT DOCUMENTS

| | | |
|---|---|---|
| EP | 0427705 | 5/1987 |
| JP | 2009-264826 | 11/2009 |

(Continued)

OTHER PUBLICATIONS

Internationaler Recherchenbericht und Schriftlicher Bescheid [International Search Report and the Written Opinion] Dated Jun. 17, 2021 From the International Searching Authority Re. Application No. PCT/EP2021/059129 and Its Translation of Search Report Into English. (11 Pages).

*Primary Examiner* — Mary Ellen Bowman
*Assistant Examiner* — Carlos Perez-Guzman

(57) ABSTRACT

The invention relates to an assembly comprising a interferometer for carrying out an optical coherence tomography, wherein the interferometer is divided into two spatially spaced-apart interferometer parts (1, 2), wherein the two interferometer parts (1, 2) can be moved related to one another and are optically connected to one another via flexible light guides (3, 4, 5), which bridge the spatial distance, wherein according to the invention, an assembly having an interferometer is provided, which is as unsusceptible as possible to the effects brought about by bending a tube cable packet and allows for an optimum signal-to-noise ratio or an optimum image quality of an OCT image, characterised in that at least one first flexible light guide (3)

(Continued)

is designed as a polarisation-maintaining light guide consisting of two connected polarisation-maintaining light-guiding fibres (3a, 3b).

5 Claims, 3 Drawing Sheets

(56) References Cited

U.S. PATENT DOCUMENTS

| | | | |
|---|---|---|---|
| 2007/0081166 A1 | 4/2007 | Brown et al. | |
| 2010/0280315 A1* | 11/2010 | Pan | G01N 21/4795 |
| | | | 356/497 |
| 2014/0098412 A1 | 4/2014 | Welford | |
| 2014/0176960 A1 | 6/2014 | Kemp | |
| 2017/0196459 A1* | 7/2017 | Lam | G01N 21/6456 |
| 2018/0184894 A1 | 7/2018 | Su | |
| 2019/0368861 A1* | 12/2019 | Wax | G01B 9/02044 |

FOREIGN PATENT DOCUMENTS

| | | |
|---|---|---|
| JP | 2015-532536 | 11/2015 |
| WO | WO 2010/044322 | 4/2010 |
| WO | WO 2019/224268 | 11/2019 |

\* cited by examiner

ASSEMBLY FOR CARRYING OUT AN OPTICAL COHERENCE TOMOGRAPHY

RELATED APPLICATIONS

This application is a National Phase of PCT Patent Application No. PCT/EP2021/059129 having International filing date of Apr. 8, 2021, which claims the benefit of priority of Germany Patent Application No. 10 2020 114 610.8 filed on Jun. 2, 2020. The contents of the above applications are all incorporated by reference as if fully set forth herein in their entirety.

FIELD AND BACKGROUND OF THE INVENTION

The invention relates to an assembly according to the preamble of claim 1.

The term optical coherence tomography (commonly abbreviated as OCT) is used to describe an imaging method. With this method, two-dimensional and three-dimensional images can be obtained from light-scattering organic tissues.

In this method, light with a large bandwidth and a temporally short coherence length is usually divided into two partial beams in a beam splitter. The first partial beam falls on the organic tissue to be examined, the second partial beam passes through a reference section. A third partial beam, namely light reflected from the organic tissue, interferes with the second partial beam in an interferometer.

Signals from the interference allow depth-resolved examination of the tissue, i.e., in the depth of the optical axis of the first partial beam. If the organic tissue is also scanned planarly or laterally with the first partial beam, three-dimensional images of the organic tissue are obtained, so-called OCT images.

Against this background, an assembly for carrying out an optical coherence tomography has become known from US 2014/0 176 960 A1, in which polarization-maintaining, light-guiding fibers without a polarization control unit are used. In this respect, interferometers with polarization-stable fibers are already known.

More generally, interferometer assemblies for carrying out an optical coherence tomography can be divided into two distinct system parts. A first system part comprises a camera head, which usually stands on a table and is directed toward the eye to be examined.

A second system part comprises at least one power supply unit arranged under the table and away from the eye. This division is chosen to keep the dimensions and weight of the camera head small, which is particularly preferred in hospitals.

A flexible hose cable package connects the power supply unit to the camera head. When handling the camera head for alignment with the eye to be examined, the hose cable package and thus also light-guiding fibers, which connect the two system parts to each other in an optically guiding manner, are bent in an uncontrolled manner.

Conventional light-guiding single-mode fibers (SMFs for short) only guide components of light rays oriented transversely to the direction of propagation.

If such fibers were used to connect the system parts, the bending of the hose cable package would introduce unpredictable polarization changes into the interferometer. This can be accompanied by a significant loss of signal-to-noise ratio and therefore a degraded image quality of an OCT image.

The invention is therefore based on the problem of specifying an assembly with an interferometer which is as insensitive as possible to the effects associated with the bending of a hose cable package and realizes the best possible signal-to-noise ratio or the best possible image quality of an OCT image.

The present invention solves the aforementioned problem by means of the features of claim 1.

First of all, it has been recognized that the aforementioned problem could be addressed, among other things, if the entire interferometer, including the light source, detectors and electronics, were combined in one housing and integrated into the camera head.

This concept would not provide a flexible hose cable package with light-guiding or optical fibers between two system parts. However, it would result in a bulky, heavy camera head. Furthermore, miniaturization and integration of all hardware components into a small-sized camera are a major technical challenge.

It was further recognized that a means could be provided to separate the interferometer into two system parts, with the camera head being very compact. The entire interferometer, the light source, the detector(s), electronic components, etc., would then be combined in a package outside the camera head.

This solution would require a flexible cable connection with optical fibers between the two system parts and could be affected by changes in polarization states and the associated losses in signal-to-noise ratio in an OCT image.

It was also recognized that the separation approach described would require active alignment of the polarization state in a system part by a mechanical or electro-optic manipulation of the polarization to reduce losses in the signal-to-noise ratio.

However, active polarization alignment is usually a very slow process and must be performed relatively frequently.

The solution proposed by the invention does not require frequent polarization alignment and is therefore not impaired by time-consuming procedures to perform it.

It has been further recognized that the entire interferometer, including the light source, the detector(s), electronic components, etc., could be integrated in a package outside the camera head. This approach would require a flexible cable connection with optical fibers between the two system parts and, as described, may be affected by changes in polarization states and the associated losses in signal-to-noise ratio in an OCT image.

In this approach, OCT signals could be split into two separate components with different polarization using polarization-sensitive optical splitters and measured by two separate detectors. Any changes in the polarization state in an interferometer result in a redistribution of the OCT signals across the two detectors without signal loss. However, this approach would require two optical detectors and the electronics associated therewith.

The measurement results would take up twice the data volume generated by the solution according to the invention. The invention, however, leads to reduced hardware costs and small amounts of data.

It was also realized that a so-called common-path interferometer could be used, which integrates the entire interferometer into a fiber-optic (coupler) path.

This particular type of interferometer integrates the arms of the interferometer, namely the sample arm and the reference arm, into a single optical path and is therefore not susceptible to losses in the signal-to-noise ratio of an OCT image due to changes in polarization.

However, it was recognized that the design of the common-path interferometer is complicated to construct for optimal OCT detection in a bulk optics-based microscope or ophthalmoscope interface, as there is no clear physical separation between the two arms of the interferometer.

For OCT microscopes and ophthalmoscopes, however, it is necessary that the length of the reference arm of the interferometer can be changed in order to be able to be adapted to the depth localization of the imaged object or to the object in the sample arm of the interferometer. This is not possible with the common-path interferometer. In addition, the split optical path in the common-path interferometer makes it more difficult to simultaneously minimize optical losses in both arms, which will always result in some form of losses in signal-to-noise ratio in the OCT images.

In the solution proposed by the invention, a Mach-Zehnder interferometer or Michaelson interferometer type configuration can preferably be used, which is precisely not associated with the problems of the common-path interferometer described above.

It was also recognized that, according to one approach, an alternative fiber-based interferometer could be used which uses polarization-maintaining light-guiding fibers (PMFs) instead of single-mode fibers (SMFs). The light passing through PMFs is not subjected to changes in polarization state when the PMF is bent or moved.

However, the physical properties of a PMF, in particular the difference between the refractive indices of the two crystal axes of this type of optical fiber, make the interferometer susceptible to ghost artefacts originating from interference between the optical signals guided via the two crystal axes.

Removing or mitigating these ghost artefacts requires complex solutions that are impracticable.

The solution proposed by the invention nevertheless uses a fiber-based interferometer based predominantly on the use of SMFs in a predominant number and a specially designed light guide, which does not produce the aforementioned ghost artefacts. Surprisingly, ghost artefacts can be avoided by connecting two polarization-maintaining light-guiding fibers to form a single light guide.

In this way, the invention creates a way to split an OCT interferometer by means of a flexible optical fiber connection into two interferometer parts, which are insensitive to a manipulation of the fiber connection.

SUMMARY OF THE INVENTION

According to the invention, it has been recognized here that the division of an interferometer into two interferometer parts and the connection of these interferometer parts can be realized while maintaining polarization stability.

According to the invention, a polarization-stable interferometer configuration for a light guide- or fiber-based optical coherence tomography is realized, which can have a compact and freely movable sample arm.

According to the invention, it is thus possible to create an assembly in which one interferometer part is designed as a manually portable, camera-based or otherwise movable interferometer part. This interferometer part has small and compact dimensions with low weight, as most of the heavier hardware parts can be placed in the other interferometer part, preferably in a separate sealed housing away from the object to be examined.

Specifically, an assembly according to the invention comprises an interferometer for carrying out an optical coherence tomography, wherein the interferometer is divided into two interferometer parts at a spatial distance from each other, wherein the two interferometer parts are movable relative to each other and are optically connected to each other by flexible light guides bridging the spatial distance. At least one of these flexible light guides is designed as a polarization-maintaining light guide which consists of two polarization-maintaining light-guiding fibers connected to each other.

This first light guide could consist of two polarization-maintaining light-guiding fibers, so-called PMFs, connected to each other, the respective crystal axes of which are tilted by 90° relative to each other. The PMFs are connected maintaining a 90° offset so that there is cross-coupling between the fiber crystal axes. This is how the first light guide, namely a so-called xPMF or cross-PMF, is created.

This first light guide surprisingly compensates the birefringence behavior of its first component with the birefringence behavior of its second component. Therefore, surprisingly, ghost patterns and fixed interference pattern artefacts, which are caused by conventional PMFs in optical coherence tomography imaging, are mitigated. The first light guide maintains a stable polarization state like a conventional PMF but can be handled or bent at will and still does not produce any artefact problems in optical coherence tomography that usual PMFs would produce.

A conventional single polarization-maintaining light-guiding fiber (abbreviated PMF or PM fiber) is designed as a single-mode fiber in which linearly polarized light is guided. As the light passes through this fiber, the polarization of the light is maintained. In such light-guiding fibers, increased birefringence is maintained so that the light can travel along the fiber in two well-defined polarization modes with clearly different phase velocities. Therefore, in a polarization-maintaining fiber, there are usually two main axes or crystal axes, a slow axis and a fast axis, along which polarized light can be transmitted while maintaining its polarization state. By tilting these two axes by 90° relative to two axes of another light-guiding fiber, ghost artefacts are avoided.

The two polarization-maintaining light-guiding fibers could be connected to each other by splicing. When two fibers are spliced, the fibers are fused or welded to each other. Preferably, no further substances are necessary to produce the connection between the fibers. From EP 0 427 705 A1 it is known how the splicing of two fibers can be carried out in principle. Preferably, the polarization-maintaining light-guiding fibers are of equal length. The birefringences of the two fibers of equal length cancel each other out or compensate for each other. The two polarization-maintaining light-guiding fibers are arranged one behind the other and connected to each other at a splice point.

At least a second and/or third light guide is or are designed as a single-mode fiber or as single-mode fibers. The second light guide and/or the third light guide can guide light from the imaging interferometer part to a detector in the other interferometer part. The light guided through these single-mode fibers does not have to be polarized or is preferably not polarized. These single-mode fibers, or SMFs for short, do not maintain a polarization state of the guided light, unlike PMFs.

Against this background, the light guides could be accommodated in a flexible hose cable which extends between the two interferometer parts. A flexible hose cable surrounds all light guides and possibly additional electrical cables in a pipe-like manner and protects them from being torn off or damaged in any other way. The flexible hose cable consists of an elastomer or a very bendable plastic so that a camera head can easily be moved by hand by bending and/or displacing the hose cable.

The first interferometer part could be assigned to a power supply unit. Thus, a relatively heavy and bulky power supply unit can be arranged as a stationary element on a stable support, preferably on a floor, while other optical elements can be moved manually relative to the first interferometer part.

Against this background, the second interferometer part could be assigned to a camera head that is movable relative to the first interferometer part. This allows the camera head to be easily directed toward an eye to be examined.

The first interferometer part could be accommodated in a first housing comprising electronic components and a power supply unit. This allows heavy objects to be accommodated in the first, stationary housing.

The second interferometer part could be accommodated in a second housing comprising the camera head. This allows the camera head to be easily directed toward an eye to be examined. It is conceivable for the second housing to form the camera head and the second interferometer part to be integrated in this housing and thus in the camera head.

The sample arm and the reference arm, along each of which light is guided, could be arranged entirely in the second housing or in the camera head. Thus, the imaging is not disturbed by the movement of the camera head.

Preferably, the assembly of the type described herein is used in ophthalmology or eye examinations.

DESCRIPTION OF SPECIFIC EMBODIMENTS OF THE INVENTION

Figure 1:
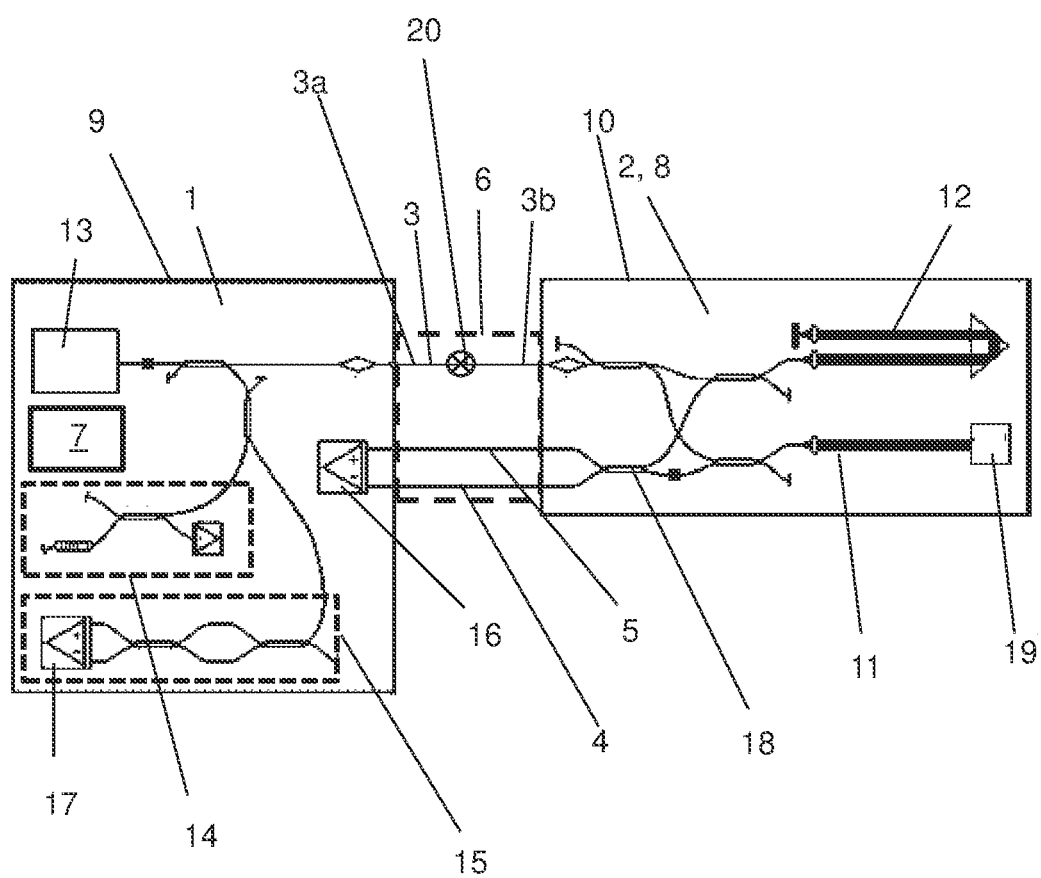
FIG. 1 shows a schematic representation of an assembly with two interferometer parts spatially separated from each other.

FIG. 1 shows an assembly comprising an interferometer for carrying out an optical coherence tomography, the interferometer being divided into two interferometer parts 1, 2 at a spatial distance from each other, the two interferometer parts 1, 2 being movable relative to each other and being optically connected to each other by flexible light guides 3, 4, 5 which bridge the spatial distance between the interferometer parts 1, 2.

At least a first flexible light guide 3 is designed as a polarization-maintaining light guide which consists of two polarization-maintaining light-guiding fibers 3a, 3b, so-called PMFs, which are connected to each other and have the same length.

The first light guide 3 consists of two polarization-maintaining light-guiding fibers 3a, 3b which are connected to each other and have the same length and the respective crystal axes 21, 22 of which are arranged tilted by 90° relative to each other at a splice point 20. This is shown schematically in FIG. 3.

The two polarization-maintaining light-guiding fibers 3a, 3b of equal length, which form the first light guide 3, are connected to each other by splicing at the splice point 20. The splice point 20 is in the middle of the light guide 3, which is formed by the two polarization-maintaining light-guiding fibers 3a, 3b arranged one behind the other and of equal length.

Furthermore, a second light guide 4 and a third light guide 5 are designed as single-mode fibers. All light guides 3, 4, 5 are accommodated in a flexible hose cable 6 which extends between the two interferometer parts 1, 2, and together with the hose cable 6 form a flexibly deformable hose cable package. The splice point 20 is positioned in the middle or approximately in the middle of the hose cable 6.

The first interferometer part 1 is assigned to a power supply unit 7. The second interferometer part 2 is assigned to a movable camera head 8.

The first interferometer part 1 is accommodated in a first housing 9 which comprises electronic components and the power supply unit 7. The second interferometer part 2 is accommodated in a second housing 10 which comprises or forms the camera head 8. The sample arm 11 and the reference arm 12 are completely and only arranged in the second housing 10 or in the camera head 8.

FIG. 1 shows specifically that the assembly is divided into two interferometer parts 1, 2, which are essentially assigned to the power supply unit 7 and the camera head 8, respectively. The first interferometer part 1 contains all the essential electronic components which comprise the light source 13 or OCT light source, trigger circuits 14 and clocking circuits 15, DAQ electronics and detectors 16, 17. The first interferometer part 1 therefore contains all or almost all electronic components that are able to be reasonably assigned to the first interferometer part 1.

Specifically, the first interferometer part 1 contains the OCT light source, namely a laser light source known to a person skilled in the art as VCSEL swept source ("Vertical Cavity Surface Emitting Laser Swept Source"), which emits light with a wavelength of 1050 nm; the trigger circuit 14, which is designed as a scan trigger circuit; the clocking circuit 15, namely a so-called K-clock circuit; DAQ electronics; and a balanced detector 16 of the interferometer.

The second interferometer part 2 is integrated into the camera head 8 and contains essentially only passive fiber components of the entire interferometer.

Three light guides 3, 4, 5 run through the flexible hose cable 6 and together with it form the flexibly deformable hose cable package to optically connect the two interferometer parts 1, 2 to each other. The first light guide 3 guides light from the light source 13, namely the OCT light source, to the camera head 8 and is made of two polarization-maintaining light-guiding fibers 3a, 3b, namely PMFs, of equal length.

PMF means "Polarization-Maintaining Fiber" and is abbreviated PMF. The first light guide 3 is created by splicing two PMFs 3a, 3b of the same length.

The second light guide 4 and the third light guide 5 guide light from the imaging interferometer part 2 in the camera head 8 to the balanced detector 16 in the first interferometer part 1 or housing 1, in which the power supply unit 7 is arranged. The balanced detector 16 is insensitive to the polarization state of the received light, and PIN diodes detect only its intensity.

Conventional single-mode fibers, which are abbreviated SMFs, are therefore used to optically connect the balanced detector 16 in the first interferometer part 1 to the two outputs of the 50/50 coupler 18 of the second interferometer part 2 in the camera head 8, although the SMFs bring about unknown changes of polarization state when they are handled or bent.

It is therefore possible to handle the second and third light guides 4, 5 at will without fear of an effect on the quality of an optical coherence tomography image. The use of these two light guides 4, 5 in combination with the first light guide 3, which maintains polarization stability, is therefore particularly advantageous.

Since the three light guides 3, 4, 5 are either insensitive to changes in polarization state, or the detection of their signals is insensitive to changes in polarization, the hose cable package can contain all three light guides 3, 4, 5 and can be moved and handled at will without fear of an effect on the signal quality of the optical coherence tomography.

The interferometer configuration described here requires a one-time adjustment and is stable in further operation. It does not require periodic or real-time polarization optimization. In addition, the space used in the camera head 8 is minimized. This optimizes the configuration of both the power supply unit 7 and the camera head 8.

Figure 2:
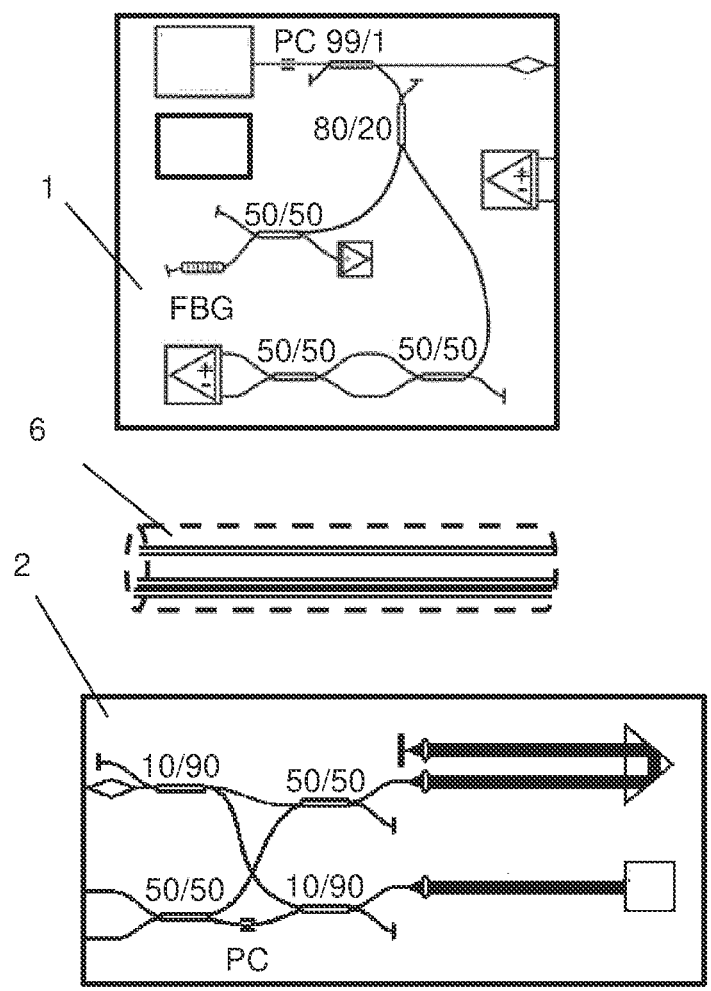
FIG. 2 shows the assembly according to FIG. 1, with the interferometer parts and the hose cable package being depicted separately.

FIG. 2 shows schematically the two interferometer parts 1, 2 and the hose cable package 6 as well as the usual electronic, optical or optoelectronic components of an interferometer familiar to a person skilled in the art.

Figure 3:
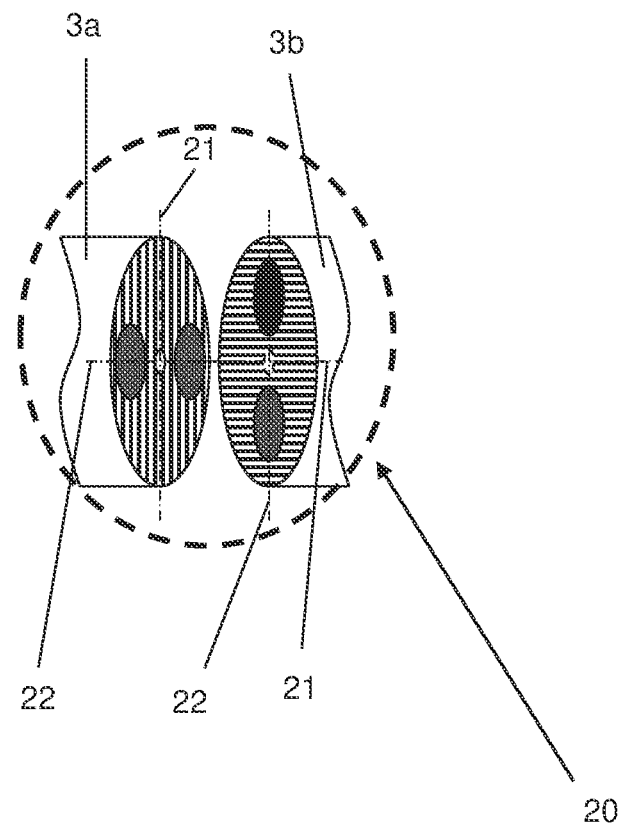
FIG. 3 shows a schematic representation of the splicing of two polarization-maintaining light-guiding fibers of equal length, the crystal axes of which are tilted by 90° relative to each other at the splice point.

FIG. 3 schematically shows by means of the splice point 20 that, when splicing the two polarization-maintaining light-guiding fibers 3a, 3b of equal length, it is necessary to match the orientations of their crystal axes 21, 22 at the splice point 20. A deliberate offset of 90°, as shown in FIG. 3, is created at the splice point 20 to achieve the birefringence compensation effect described here.

A PM fiber fusion splicer, not shown, typically has a device for suitably rotating and aligning relative to each other polarization-maintaining light-guiding fibers to be connected.

LIST OF REFERENCE SIGNS

1 First interferometer part
2 Second interferometer part
3 First light guide
3a, 3b Polarization-maintaining light-guiding fiber
4 Second light guide
5 Third light guide
6 Flexible hose cable
7 Power supply unit
8 Camera head
9 First housing
10 Second housing
11 Sample arm
12 Reference arm
13 Light source
14 Trigger circuit
15 Clocking circuit
16 Balanced detector 16
17 Further detector
18 50/50 coupler
19 Scanning unit
20 Splice point
21 First crystal axis
22 Second crystal axis

The invention claimed is:

1. An assembly comprising:
first and second housings (9) (10); and
an interferometer for carrying out an optical coherence tomography,
wherein the interferometer is divided into two interferometer parts (1, 2) at
a spatial distance from each other;
wherein the two interferometer parts (1, 2) are movable relative to each other and are optically connected to each other by at least one flexible light guide (3, 4, 5) which bridges the spatial distance;
wherein the first housing (9) comprises:
the first interferometer part (1), comprising:
electronic components; and
a power supply unit (7);
wherein the second housing (10) comprises:
the second interferometer part (2), comprising:
a camera head (8), comprising:
a sample arm (11);
a reference arm (12); and
a plurality of single-mode fiber light guides leading to
the sample arm (11) and to the reference arm (12);
wherein the at least one flexible light guide comprises a flexible light guide designed as a polarization-maintaining light guide which consists of two polarization-maintaining light-guiding fibers (3a, 3b) connected to each other;
wherein the respective crystal axes of which are arranged tilted by 90° relative to each other.

2. The assembly as claimed in claim 1, wherein the two polarization-maintaining light-guiding fibers (3a, 3b) are connected to each other by splicing and/or are of equal length.

3. The assembly as claimed in claim 1, wherein the at least one flexible light guide comprises one or more light guides designed as a single-mode fiber or as single-mode fibers.

4. The assembly as claimed in claim 1, wherein the at least one flexible light guide is accommodated in a flexible hose cable (6) which extends between the two interferometer parts (1, 2).

5. The assembly as claimed in claim 1, wherein the sample arm (11) and the reference arm (12) are arranged in the camera head (8).

* * * * *